United States Patent [19]

Stiegelmann et al.

[11] Patent Number: 5,533,800
[45] Date of Patent: Jul. 9, 1996

[54] PROCEDURE AND APPARATUS FOR DETECTING VISCOSITY CHANGE OF A MEDIUM AGITATED BY A MAGNETIC STIRRER

[75] Inventors: René Stiegelmann, Staufen; Erhard Eble, Bad Krozingen-Tunsel; Helmut Siegel, Bad Krozingen, all of Germany

[73] Assignee: Janke & Kunkel GmbH & Co. KG IKA-Labortechnik, Staufen, Germany

[21] Appl. No.: 336,448

[22] Filed: Nov. 9, 1994

[30] Foreign Application Priority Data

Nov. 19, 1993 [DE] Germany ............... 43 39 328.4

[51] Int. Cl.⁶ ................................................. B01F 13/08
[52] U.S. Cl. ................................. 366/142; 366/274
[58] Field of Search .............................. 366/142, 273, 366/274, 143, 348, 349; 422/68.1, 99, 108, 119

[56] References Cited

U.S. PATENT DOCUMENTS

| | | | |
|---|---|---|---|
| 4,390,283 | 6/1983 | Meyer | 366/142 |
| 4,876,069 | 10/1989 | Jochimsen | 366/274 |

FOREIGN PATENT DOCUMENTS

| | | |
|---|---|---|
| 2687223 | 8/1993 | France . |
| 1804292 | 12/1972 | Germany . |
| 2929437 | 2/1980 | Germany . |
| 156144 | 8/1982 | Germany . |
| 2366207 | 5/1984 | Germany . |
| 3322409 | 1/1985 | Germany . |

OTHER PUBLICATIONS

Derwent Publications Ltd., Section El, Week 9207, *Gorki Univ. Phys. Tec.*, SU–398594, (1991).
Derwent Publications Ltd., Section Ch, Week 8831, *Gakken KK*, AN 88–216145, (1988).

*Primary Examiner*—Robert W. Jenkins
*Attorney, Agent, or Firm*—Panitch Schwarze Jacobs & Nadel

[57] ABSTRACT

A magnetic stirrer (1) with a magnet (3) driven in a rotating fashion by an electric motor (2) for the activation of a stirring bar magnet (7) inside a container (5) filled with a medium (6) has a digitally operated regulator (8), implemented with software, that is a software regulator. With this regulator, the rotational drive speed of the motor (2) can be held constant. At the same time, the change in the regulated quantity of this regulator (8) is detected and, in the event of a change in load, is reported to or displayed for the user as a trend or tendency of the viscosity change of the medium (6). In this way, the regulation of a constant rotational motor speed can be used at the same time for detecting changes in viscosity of the stirred medium (6).

13 Claims, 1 Drawing Sheet

PROCEDURE AND APPARATUS FOR DETECTING VISCOSITY CHANGE OF A MEDIUM AGITATED BY A MAGNETIC STIRRER

FIELD OF THE INVENTION

The invention pertains to a procedure for the detection of the change in viscosity of a medium stirred in a container by means of a magnetic stirrer, in which a stirring magnet in the medium is set into rotation by means of a magnet being rotated underneath the container with the aid of a drive motor, the magnet being magnetically coupled with the stirring magnet.

The invention further pertains to an apparatus with a magnetic stirrer for carrying out this procedure, in which a magnet driven in a rotating fashion with the aid of a drive motor sets into rotation, by means of magnetic coupling, a stirring magnet inside a container for a medium.

BACKGROUND OF THE INVENTION

Magnetic stirrers with a rotatable magnet driven by a drive motor are known. Upon activation, this rotatable magnet is magnetically coupled with a stirring magnet. This stirring magnet is placed within a container with the medium that is to be stirred and is, as a rule, located above the rotatable magnet.

In conjunction with such stirrers it is also known that during the stirring procedure the viscosity of the medium or fluid can increase or decrease. Often, such changes in viscosity are actually so slight that they cannot be detected at all or are detected only very inexactly through use of conventional means and methods. Up until now, for example, a test sample is taken from the stirring container, its viscosity measured, and the entire sample then poured back into the container so that the total quantity of stirred fluid in the stirring container is not altered. During the removal and transfer of the test sample to a measurement site, however, additional changes in viscosity can also take place, so that an inaccurate measurement may result. In addition, the removal itself of the test sample and its pouring back can in turn lead to slight changes in viscosity.

It is, of course, already known that the current consumption of drive motors can be measured, and thus a change in the power consumption can be detected in the event of load changes. However, this is only successful when relatively large changes in the load take place. Since, however, in the case of viscosity variations and, above all, small changes in viscosity of the liquid to be stirred, the load changes on such a drive motor for a magnetic stirrer can be much smaller than, for example, the network variations of the power supply, a reliable value for the tendency of a change in viscosity cannot be attained in this way.

From DE-AS 1 804 292 an apparatus is known for the determination of the prothrombin time of blood plasma, an apparatus that is based on the fact that during the coagulation of the blood plasma, a stirring magnet is prevented from further rotation as a result of the increasing viscosity, so that with the aid of an inductive circuit element, an electrical signal can be generated in order to indicate this point in time. In this way, however, only the coagulation of the blood plasma can be indicated, and not a very slight change in the viscosity. Above all, the tendency of a change in viscosity cannot be determined in this way.

From DE 23 66 207 C2 an apparatus is known for the measurement of cure times, particularly for plastic resins of different generic types, in which a stirring head is placed at a location provided with a rotating drive. A disconnect device for the rotating drive as well as a timer, is provided that switches when there is a sharp increase in the stirring resistance. In conjunction with this, a disconnect apparatus is also provided that activates at a pre-determined limit value during the increase in current consumption of the rotating drive resulting from the increase in the stirring resistance. The tendency of a change in viscosity cannot be reliably determined in this way either.

SUMMARY OF THE INVENTION

An object of the invention is therefore to create a procedure, starting from the art described at the beginning, as well as an apparatus for carrying out this procedure, by means of which a user can at any time determine whether the viscosity of the stirred medium is increasing, decreasing, or staying the same.

To achieve this object, the procedure mentioned at the beginning is used, in which the speed of rotation of the drive motor is held constant via regulation, and during changes in load, the change in the regulated quantity of the regulator is detected and displayed.

Thus, it is not the current consumption of the motor that is measured, which would not lead to usable values, but, in a surprising and advantageous way, it is changes in the regulator that are detected, since during a heavier load on the drive motor, that is when there is an increase in viscosity, more current must be made available to the drive motor, while in the case of a decrease in the viscosity, and the lower loading of the drive motor that accompanies it, the regulator must similarly allow a correspondingly smaller amount of current to flow through. The changes in the regulated quantity that take place at the regulator thus yield a reliable value for detecting a change in viscosity.

An especially precise detection as well as display of a change in viscosity is made possible if a digitally operated regulator is used that is implemented by means of software. With a regulator of this type, which is itself known, the disturbance variables can be fully stabilized in a very economical way on the one hand, and on the other, the changes in the regulated quantity can be measured, recorded, and displayed in a very simple way, again advantageously by means of appropriate software.

In addition, the apparatus with a magnetic stirrer, mentioned at the beginning for carrying out this procedure, serves to achieve this object wherein the magnetic stirrer has a digitally operated regulator, implemented by means of software, for the rotation speed of the drive motor, and between the regulator and the drive motor there is connected an evaluation device for the detection and display of the change in regulated quantity of the regulator.

Digitally operated regulators that are implemented by means of software, also known as "software regulators", are known per se. If a regulator of this type is now used for a magnetic stirrer and its drive motor, it is thus possible to detect, through inexpensive means, when and if this regulator must come into operation in order to compensate for changes in load on the drive motor and to keep this drive motor at a constant speed of rotation. At the same time, changes that arise at the regulator can be detected and made known, such as a tendency of change of viscosity.

In conjunction with this, it is advantageous if the evaluation device has allocated thereto a filter that eliminates or suppresses brief variations in the regulated quantity. In this way, a precise evaluation of the change in regulated quantity during changes in load can be detected and displayed, without a false picture being provided by brief variations in the regulated quantity that are not caused by changes in viscosity. A display of the tendency or trend of the viscosity is thus made available to the user.

A further development of the invention can reside in the fact that a detection of the change in the regulated quantity is preferably provided before the filter of the evaluation device. In this way, it is possible to determine or detect whether the magnetic coupling between the stirring magnet and the rotating magnet of the magnetic stirrer has been broken. If this magnetic coupling has in fact been interrupted, the drive motor constantly makes rotating movements of varying speed, which the regulator attempts to compensate for, so that a very large number of changes in the regulated quantity arises. These numerous changes in the regulated quantity can then be evaluated as a sign that the coupling between the driven magnet and the stirring magnet has been broken.

By these means, it is particularly helpful that the user of a magnetic stirrer can obtain important additional information with regard to changes in viscosity on the one hand, and with regard to the magnetic coupling on the other, without expensive additional apparatus parts or aggregates which have corresponding space requirements and have to be housed inside the magnetic stirrer.

BRIEF DESCRIPTION OF THE DRAWING

The foregoing summary, as well as the following detailed description of a preferred embodiment of the invention, will be better understood when read in conjunction with the appended drawings. For the purpose of illustrating the invention, there is shown in the drawings an embodiment which is presently preferred. It should be understood, however, that the invention is not limited to the precise arrangements and instrumentalities shown. In the drawings, which are partially schematic.

DETAILED DESCRIPTION OF PREFERRED EMBODIMENTS

Figure 1:
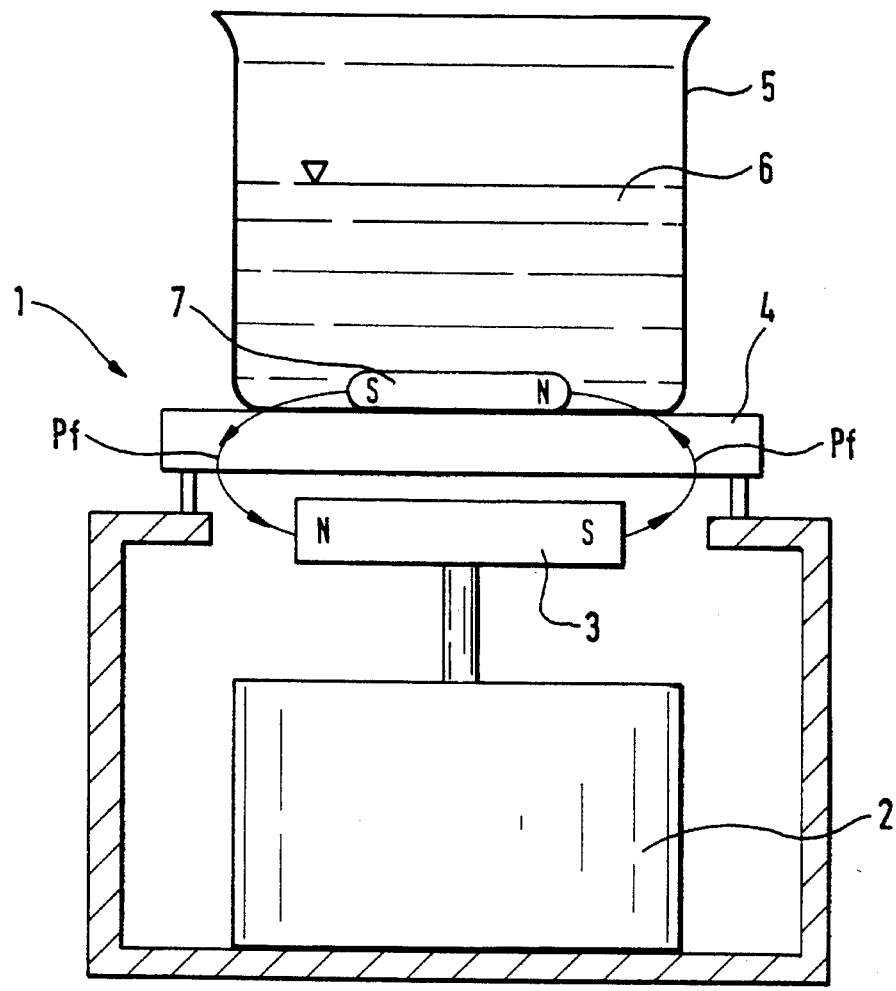
FIG. 1 shows a magnetic stirrer with a drive motor that drives a rotatable permanent magnet, and with a mounting plate for example a heating plate, on which a container with a fluid can be placed, in which a stirring magnet is positioned that is magnetically coupled with the driven rotating magnet during operation.

A magnetic stirrer, which is designated in its entirety by 1, has an electric motor as the drive motor 2 for a rotating magnet 3. Above this rotating magnet 3 is located a mounting plate 4, which can also be a heated plate. On this plate 4 there can be placed a container 5, for example a glass beaker, with a medium 6 that can be stirred by means of a bar magnet 7 which is placed into the medium 6 and that is magnetically coupled with the rotating magnet 3, as is indicated by the arrow Pf in FIG. 1.

Figure 2:
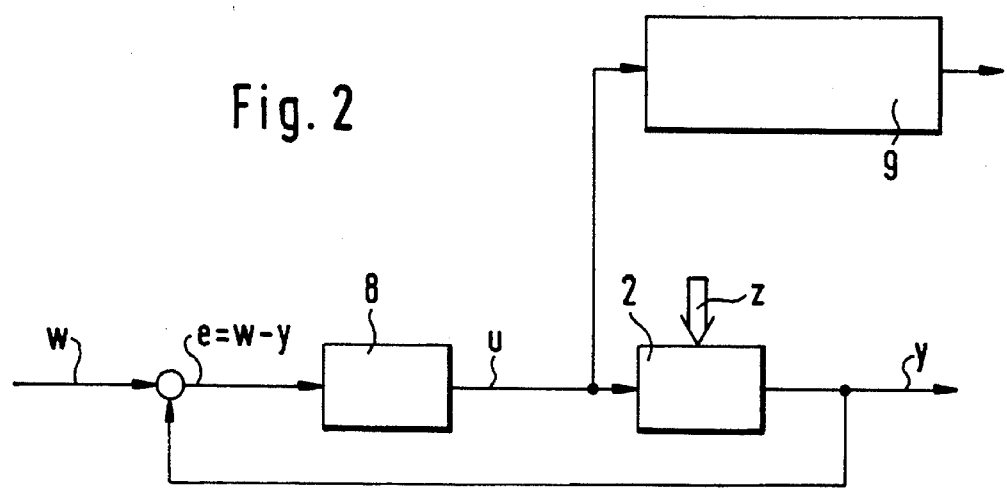
FIG. 2 is a schematic representation of the means of regulating the motor's speed of rotation and the means of detecting the tendency of the viscosity of the stirred medium.

To control the drive motor 2, as is shown in FIG. 2, there is a regulating circuit which carries out the regulation of rotational speed with the aid of a speed regulator 8. In this way the actual rotation speed of the drive motor 2 and the rotating magnet 3, as well as the bar magnet 7, can be made to follow the desired speed of rotation with no considerable regulating deviations. The regulated quantity u, which is output by the regulator 8 and acts upon the drive motor 2, namely brings about the supply of power to the drive motor 2, is determined by the efficiency of the drive motor, the speed of rotation, the size of the bar magnet 7, and the viscosity of the medium 6.

Usually in this process, the command variable w, which is, for example, the desired speed of rotation, is input into this regulating circuit. This is then usually compared, before the regulator 8, with the output quantity or the actual value y of the process or the drive motor 2, which yields as the difference between the desired rotation speed and the actual rotation speed, the regulating deviation e, which is input into the regulator 8. In this way, the regulator 8 can react appropriately to such a regulating deviation, or difference between the desired and actual rotation speeds.

In addition, a disturbance value z, for example in form of a change in viscosity or even a breaking of the magnetic coupling between the rotating magnet 3 and the bar magnet 7, can have an influence on the entire process, or to be more specific, on the drive motor 2 and its rotation speed, which changes the output quantity y correspondingly and then has an effect once again, as a regulating deviation, on the regulator 8.

If a constant rotation speed of the drive motor 2 is maintained by the regulator 8, which is advantageously configured as a software regulator, the regulated quantity u is influenced exclusively by the viscosity of the medium 6 in the container 5. If the viscosity increases, then the regulated quantity increases as well. If the viscosity decreases, then the regulated quantity decreases as well.

The user can now decide, for example by a push of a button, from which point in time a change in the viscosity of the medium 6 should be measured. At the moment the button is pushed, the momentary viscosity is thus selected as the reference value against which a change is to take place and be detected in the remaining course of the operation. In conjunction with this, one can see in FIG. 2 that between the regulator 8 and the drive motor 2, the regulated quantity is detected and is sent to an evaluation device 9. If a change in the regulated quantity takes place, it can thus be detected and displayed by the evaluation device 9. In this way, a change in the regulated quantity of the regulator 8 during a load change can be noted, and can be displayed as a tendency or trend in viscosity change. A relative change in the regulated quantity is thus used advantageously as an indicator of the change in viscosity.

In this case, a filter is allocated to the evaluation device 9 that eliminates or suppresses brief deviations in the regulated quantity, so that no erroneous measurements will result from brief deviations of this type.

One thus proceeds with the magnetic stirrer 1 to hold constant the rotational drive speed of the drive motor 2 with the aid of the regulator 8, and detects and displays the changes in the regulated quantity by the regulator 8 during a change in load. Specifically, these changes are detected and displayed as a trend or tendency of a change in viscosity. Possibly, a display device can be provided that indicates directly in percentages what the change in viscosity is during a current operating state, in comparison with an initial state that was selected by the push of a button.

In the case of a very high viscosity, it can happen that the magnetic coupling between the bar magnet 7 and the rotating magnet 3 breaks. This condition can be detected and evaluated by means of a sudden decrease and a very strong variation in the relative change of regulated quantity, whereby it is advantageous if this takes place before the filter of the evaluation device 9.

If a regulator 8 is used which is implemented with software and digitally operated, the change in the regulated quantity can be detected in a very simple way, without requiring special additional parts which can be space consuming. In this way, the entire magnetic stirrer 1, in spite of this additional ability to display changes in viscosity, is scarcely more costly, and most importantly, scarcely any larger than a conventional magnetic stirrer with a software regulator for the rotation speed of the drive motor 2. For this purpose, it is possible, above all, that the evaluation device 9 for the change in regulated quantity of the regulator 8 be connected between the regulator 8 and the actual process, that is the regulated drive motor.

On the whole, a very precise evaluation of the change in the regulated quantity during a change in the load thus results via very inexpensive means. This evaluation can be used in order to carry out a display of the trend or tendency of the viscosity in the stirred fluid. Thus, in order to determine if the viscosity of the medium 6 increases, decreases, or remains the same during the stirring procedure, no test samples of the medium need be taken and subjected to a time-consuming measurement.

The magnetic stirrer 1 with a magnet 3 driven in a rotating fashion by an electric motor 2 for activation of a stirring bar magnet 7 inside a container 5 filled with a medium 6 has a digitally operated regulator 8 implemented with software, that is a software regulator. With this regulator the rotational drive speed of the motor 2 can be held constant. At the same time, the change in regulated quantity of this regulator 8 is detected and, in the event of a change in load, is reported to or displayed for the user as a trend or tendency of the change in viscosity of the medium 6. In this way, the regulation of a constant rotational motor speed can be used for detecting changes in viscosity of the stirred medium 6 at the same time.

It will be appreciated by those skilled in the art that changes could be made to the embodiment described above without departing from the broad inventive concept thereof. It is understood, therefore, that this invention is not limited to the particular embodiment disclosed, but it is intended to cover modifications within the spirit and scope of the present invention as defined by the appended claims.

We claim:

1. A procedure for detection of a change in viscosity of a medium (6) stirred in a container (5) by means of a magnetic stirrer (1), comprising rotating a stirring magnet (7) in the medium (6) by means of a drive motor (2) which drives a magnet (3) that is rotated underneath the container (5) and is magnetically coupled with the stirring magnet (7), holding the speed of rotation of the drive motor (2) constant by means of regulation, and during changes in load on the magnet (3) detecting and displaying changes in the regulation.

2. The procedure according to claim 1, wherein regulation is effected by a digitally operated regulator (8).

3. The procedure according to claim 2, wherein the regulator (8) is implemented by software.

4. The procedure according to claim 1, wherein changes in load which can be detected also include an interruption in the magnetic coupling between the magnet (3) and the stirring magnet (7).

5. The procedure according to claim 1, wherein changes in load are detected by detecting changes in a regulated quantity of a regulator.

6. The procedure according to claim 1, wherein detection of brief variations in the load is eliminated or suppressed by filtration before displaying changes in the regulation.

7. The procedure according to claim 6, wherein an interruption in the magnetic coupling between the magnet (3) and the stirring magnet (7) is detected and displayed prior to said filtration.

8. A magnetic stirring apparatus comprising a rotating magnet (3) driven by a rotating drive motor (2) at a desired speed of rotation, a stirring magnet (7) inside a container (5) for a medium (6), said stirring magnet (7) being magnetically coupled to said rotating magnet (3), the rotating magnet (3) being located in proximity to a bottom portion of the container (5), a regulator (8) for the drive motor's (2) speed of rotation, and connected between the regulator (8) and the drive motor (2) an evaluation device (9) for the detection and display of a change in a regulated quantity of the regulator (8).

9. The apparatus according to claim 8, wherein the regulator (8) is a digitally operated regulator.

10. The apparatus according to claim 8, wherein the regulator (8) is implemented by means of software.

11. The apparatus according to claim 8, wherein the evaluation device (9) further includes a filter that eliminates or suppresses brief variations in the regulated quantity.

12. The apparatus according to claim 8, further comprising means for detection and/or display of a change in the regulated quantity resulting from breaking of the magnetic coupling between the stirring magnet (7) and the rotating magnet (3).

13. The apparatus according to claim 12, wherein said means for detection and/or display is connected in front of a filter for eliminating or suppressing brief variations in the regulated quantity.

* * * * *